United States Patent [19]

Edwards et al.

[11] Patent Number: 5,589,500
[45] Date of Patent: Dec. 31, 1996

[54] SUBSTITUTED 1,1,2-TRIPHENYLBUTENES AND THEIR USE IN THE TREATMENT OF CANCER

[75] Inventors: Karen J. Edwards, Natal, South Africa; Michael Jarman, Tooting, England; Charles A. Laughton, Sutton, England; Stephen Neidle, Oxhey, England; Ian R. Hardcastle, Sutton, England

[73] Assignee: British Technology Group Limited, London, England

[21] Appl. No.: 331,582

[22] PCT Filed: Apr. 29, 1993

[86] PCT No.: PCT/GB93/00889

§ 371 Date: Jan. 17, 1995

§ 102(e) Date: Jan. 17, 1995

[87] PCT Pub. No.: WO93/22275

PCT Pub. Date: Nov. 11, 1993

[30] Foreign Application Priority Data

May 1, 1992 [GB] United Kingdom .................. 9209509
Feb. 26, 1993 [GB] United Kingdom .................. 9303982

[51] Int. Cl.$^6$ .................. C07C 217/18; C07D 295/088; A61K 31/135; A61K 31/40
[52] U.S. Cl. .................. 514/428; 514/648; 548/570; 564/324
[58] Field of Search .................. 548/570; 564/324; 514/428, 648

[56] References Cited

FOREIGN PATENT DOCUMENTS

| | | |
|---|---|---|
| 0260066 | 3/1988 | European Pat. Off. . |
| 2196003 | 4/1988 | United Kingdom . |

OTHER PUBLICATIONS

D. W. Robertson et al., "Antiestrogen Bascity—Activity Relationships . . . ", J. Med. Chem. 25, 167–171 (1982.

M. G. Rowlands et al., "Variation on the inhibitions of calmodulin dependent cyclic AMP phosphodiesterase . . . ", Biochemical Pharmacology 40, 283–289 (1990).

A. Bouhoute and G. Le Clercq, "Antagonistic effect of triphenylethylenic antiestrogens . . . ", Biochem. Biophys. Res. Comm. 184, 1432–1440 (May 15, 1992).

C.D.M.A. Van den Koeduk et al., "Comparative affinity of steroidal and non-steriodal antioestrogens . . . ", Biochem. Pharm. 43, 2511–2518 (1992).

R. McCague et al., "The iodine atom in 4–iodotamoxifen reduces the extent of metabolism . . . ", Brit. J. Cancern 62, 505 (1990).

B. P. Haynes et al., "Metabolism and pharmacokinetics of pyrrolidino–4–iodotamoxifen inthe rat", Breast Cancer Research and Treatment 19, 174 (1991).

M. G. Rowlands et al., "Idoxifene (pyrrolidino–4–iodotamoxifen)–a new antiestrogen . . . ", Annals of Oncology, 157, (1992).

S. K. Chander et al., "Pyrrolidino–4–iodotamoxifen and 4–iodotamoxifen, new analogues of the antioestrogen tamoxifen . . . " Annals of Oncology, 157, (1992).

S. Y. Loh et al., "The effect of calmodulin inhibitors on cisplatin-sensitive and –resistant human ovarian carcinoma cell lines", (abstract P173), Brit. J. Cancer. 67, 74 (1993).

R. McCague et al., "Metabolism of the 4–iodo derivatives of tamoxifen by isolated rat hepatocytes", Biochem. Pharmacol. 40, 2277–2283 (1990).

K. J. Edwards et al., "A molecular modelling study of the interactions between the antiestrogen drug tmoxifen and several derivatives . . . ", J. Med. Chem. 35, 2753–2761 (1990).

R. C. Coombes et al., "New endocrine agents for the treatment of breast cancer" Recent Results in Cancer Research, 127, 267–275, (1993).

*Primary Examiner*—Robert Gerstl
*Attorney, Agent, or Firm*—Nixon & Vanderhye

[57] ABSTRACT

Compounds of the general formula (2)

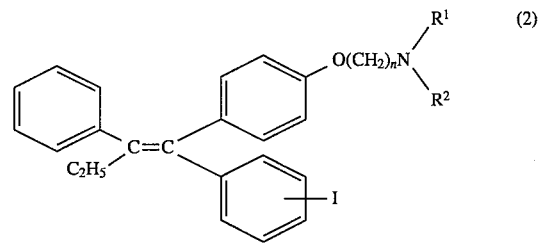

wherein n is an integer of from 3 to 10, the iodo substituent is in the 3- or 4-position and $R^1$ and $R^2$, which may be the same or different, represent $C_{1-3}$ alkyl, especially methyl or ethyl, groups or $R'$ represents a hydrogen atom and $R^2$ a $C_{1-3}$ alkyl group or $R^1$ and $R^2$ together with the nitrogen atom to which they are attached represent a saturated heterocyclic group, especially a pyrrolidino group, in the form of their free bases or pharmaceutically acceptable acid addition salts are potent anti-oestrogenic compounds useful for treatment of oestrogen-dependent cancers, especially breast cancers. Compounds where the iodine atom is radioisotopic are useful in radiotherapy or gamma ray imaging of these cancers.

13 Claims, No Drawings

SUBSTITUTED 1,1,2-TRIPHENYLBUTENES AND THEIR USE IN THE TREATMENT OF CANCER

This application is a 371 of PCT/GB 93/00889 filed Apr. 29, 1993.

BACKGROUND OF THE INVENTION

1. Field of the Invention

The invention relates to substituted 1,1,2-triphenylbutenes which are structurally related to tamoxifen, a drug used in the treatment of oestrogen-dependent cancer, especially breast cancer, and their use for the same purpose.

2. Background of the Inventions

Researchers into anti-cancer drugs continually seek to improve on existing drugs, in particular to increase their efficacy. Many variations of the structure of tamoxifen have already been proposed. One such proposal is contained in our U.S. Pat. 4,839,155. (The European counterpart is EP-B 260 066). This patent claims 3- and 4-iodotamoxifen derivatives of formula (1):

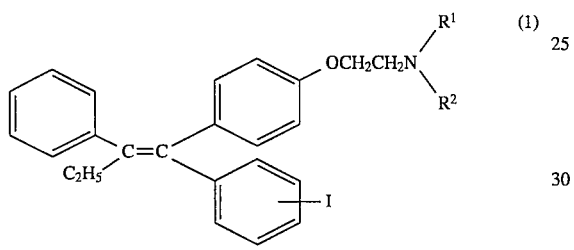

wherein I represents a 3- or 4-iodo substituent and $R^1$ and $R^2$, which may be the same or different, represent $C_{1-3}$ alkyl groups or $R^1$ represents a hydrogen atom and $R^2$ a $C_{1-3}$ alkyl group and $R^1$ and $R^2$ together with the nitrogen atom to which they are attached represent a saturated heterocyclic group, in the form of the free bases or their pharmaceutically acceptable acid addition salts. Preferably $R^1$ and $R^2$ represent methyl groups or $R^1$ and $R^2$ together with the said nitrogen atom, represent a pyrrolidino group. The most preferred such compounds have the iodine atom in the 4-position of the phenyl group and are termed "4-iodo tamoxifen" and "Idoxlfene" respectively.

SUMMARY OF THE INVENTION

It has now been found that extending the ethylene (—$CH_2$—$CH_2$—) part of the side-chain of such compounds confers on representative compounds benefits over tamoxifen, and even over 4-iodotamoxifen or Idoxifene, from which it can reasonably be concluded that they will be particularly valuable for treatment of oestrogen-dependent cancer, especially breast cancer.

Accordingly, the present invention provides compounds of the general formula (2)

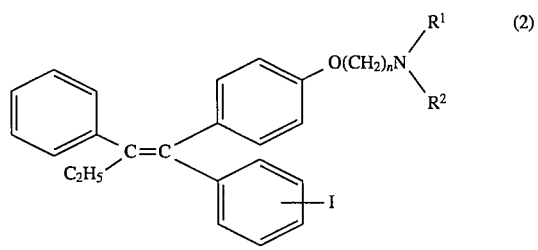

wherein n is an integer of from 3 to 10, I represents a 3- or 4-iodo substituent and $R^1$ and $R^2$, which may be the same or different, represent $C_{1-3}$ alkyl groups or $R^1$ represents a hydrogen atom and $R^2$ a $C_{1-3}$ alkyl group or $R^1$ and $R^2$ together with the nitrogen atom to which they are attached represent a saturated heterocyclic group and their pharmaceutically acceptable acid addition salts.

The invention also includes compounds of formula (2) for use in the treatment of said cancers, most particularly in humans.

Compounds of formula (2) in which the iodine atom is radioisotopic are included in the invention, as well as their use in treating the said cancers by radiotherapy or in diagnosing them, according to the isotope employed.

The invention further provides a pharmaceutical composition comprising a compound of formula (2) in association with a pharmaceutically effective diluent or carrier.

D. W. Robertson et al, J. Med. Chem. 25, 167–171 (1982) showed that the chain-extended, unsubstituted pyrrolidino tamoxifen of formula (3)

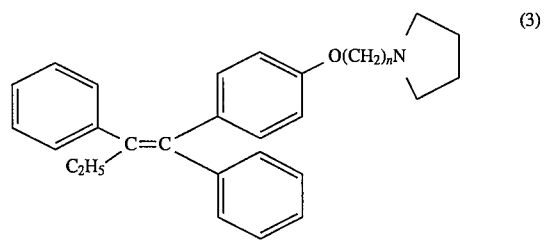

wherein n=3, has a lower binding affinity for the oestrogen receptor, as measured in a rat uterine cytosol competitive binding assay, than pyrrolidino tamoxifen itself (n=2). Such evidence has dissuaded researchers from experimenting with chain extension of tamoxifen derivatives and points away from the present invention.

DESCRIPTION OF THE PREFERRED EMBODIMENTS

The 4-iodo derivatives are preferred to the 3-iodo. Preferably $R^1$ and $R^2$ are both alkyl groups, most preferably methyl or ethyl, or $NR^1R^2$ is pyrrolidino. Preferably n is from 3 to 8, most preferably from 3 to 6.

The compounds of formula (2) and their salts can be prepared starting from ketones which are easily preparable analogues of known compounds. The ketone is reacted with an organometalltc reagent derived from 1,3- or 1,4-diiodobenzene and capable of addition to a ketone group, in a substantially anhydrous organic solvent, to form a tertiary alcohol which is then dehydrated to eliminate a molecule of water and thereby provide the ethylenic double bond required. The preferred reagent for the preparation of the organometallic iodobenzene species is n-butyllithium. Alternatively the magnesium Grignard reagent can be used. The dehydration is preferably carried out by heating the alcohol in a strong acid such as concentrated hydrochloric acid. A mixture of isomers is normally produced, of which the desired one is that in which the ethyl group and the (aminoalkoxy)phenyl group are trans.

In a preferred method of preparation, the starting ketone contains the 4-(ω-chloroalkoxy)phenyl group. The dehydration to the olefin yields the (ω-chloroalkoxy)phenyl intermediate. The isomers can often be separated by crystallisation, which is very convenient, and the desired isomer appropriately aminated by reaction with the alkylamine required. The amination can be carried out in any manner known in the synthesis of tamoxifen, for example heating the chloroethoxy intermediate with the amine, such as methylamine or pyrrolidine, in a sealed vessel.

In an alternative method of the invention, the starting ketone already contains the 4-(ω-aminoalkoxy)phenyl group and therefore the whole reaction can be carried out "direct" in one step (since the tertiary alcohol need not be isolated). The isomer separation is then carried out on the end product.

Further details of the above methods of preparation can be derived from our said prior patent, substituting side-chain-extended starting compounds for the chloroethoxy or aminoethoxy compounds therein described.

If, for a particular compound, neither of the above methods gives a satisfactory separation of isomers, as was found when attempting to prepare the compound of formula (2) in which n is 4, I is 3-iodo and $R^1$, $R^2$ and the N-atom together represent pyrrolidino, then it is suggested to proceed via an olefin intermediate which contains a bulky ether group in the benzene ring, at the 4-position, where the aminoalkoxy side-chain is to be present in the final compound. The perfluorotolyloxy ether is suggested. The isomers of this intermediate are separated, the bulky ether group is removed from the desired isomer to give the 4-hydroxyphenyl compound, which is then converted in a known manner, e.g. via the 4-(ω-chloroalkoxy) phenyl derivative, to the desired compound of formula (2). A reaction scheme is shown in Examples 6 and 7 which can readily be adapted mutatis mutandis for the preparation of other compounds of formula (2).

The acid addition salts can be prepared in any manner analogous to those of tamoxifen, at any appropriate stage of the overall synthesis after formation of the tertiary alcohol. Usually they will be prepared as the final stage or by conversion of the final compounds. Examples of such salts are the hydrochloride, sulphate, phosphate, acetate and citrate. In the "direct" method of preparation, an acid addition salt is formed under the acidic dehydration conditions used. This will ordinarily be neutralised with, say, sodium hydroxide. The isomers can then be separated either as the free bases or, after adding a approximately stoichiometric proportion of acid, as acid addition salts.

For pharmaceutical formulation, the compounds of formula (2) can be formulated in the same or a similar way to tamoxifen and administered similarly and in about the same dose. Preferably they are formulated as tablets.

The compounds of formula (2) include those wherein the iodine atoms in some or all of the molecules of a given sample have a radioisotoplc (a radioactive or "hot") iodine atom. Predominantly useful such atoms are $^{125}I$ which emits low energy electrons having a short, sub-cellular range and $^{131}I$ and $^{123}I$ which emit gamma rays. The $^{125}I$ isotopic iodine is useful in the therapy of rumour cells containing oestrogen receptors.

The $^{123}I$ and $^{131}I$ isotopes, of which $^{131}I$ is preferred, are gamma emitters and therefore usable for imaging of oestrogen receptor-carrying rumour cells. The content of radioisotopic iodine in the iodotamoxifen formulation should be adjusted to conform to conventional radiotherapy and imaging practice.

The commonly used radioisotopes of iodine have a short half-life, for $^{131}I$ 8 days, for $^{125}I$ 60 days, and for $^{123}I$ 13 hours. It is therefore necessary to prepare the radioisotopic compounds of the invention only shortly before the expected time of use.

The radioisotopic iodotamoxifen derivatives can be prepared by a process comprising reacting a compound of formula (4)

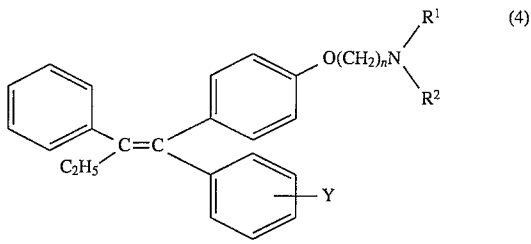

wherein n, $R^1$ and $R^2$ are as defined in connection with formula (2) and Y represents a 3- or 4-substituent, whether an atom or a group, capable of being cleaved from its benzene ring (including within this definition a non-radioisotopic iodine atom), with a reagent capable of effecting such cleavage and with a source of radiotsotopic iodine (which can be added as molecular iodine or iodide ions according to the cleavage-effecting reagent used and other reaction conditions). Preferably Y is chloro, bromo, non-radioisotopic iodo or amino. Compounds of formula (4) can be prepared by methods analogous to those described in our said prior patent.

Further details of preparation of the radioisotopes are given in our said prior patent and analogous methods can be used in the present context.

The following Examples illustrate the invention. Examples 1–5 describe the preparation of compounds of the invention. Example 6 describes tests relevant to their utility. "Ether" is diethyl ether.

All reactions performed under an inert atmosphere were carried out in oven dried glassware (110° C., 24 h.) "Ether" refers to diethyl ether. "Petrol" refers to the fraction with the boiling range 60°–80° C. Anhydrous tetrahydrofuran (THF) was obtained by distillation from potassium and benzophenone. "Brine" refers to saturated aqueous sodium chloride solution. The silica used in chromatography was Merck 15111.

Note that although tamoxifen itself is designated as the Z geometric isomer, the analogues prepared in these examples, although having the analogous sterochemistry in which the ethyl group and the nitrogen-containing side-chain are trans with respect to the central double bond, are designed as E.

EXAMPLE 1

(a) Preparation of 3-Chloropropoxybenzene

A two-phase mixture of phenol (5 g, 53 mmol), dichloropropane (32 ml), tetrabutylammonium hydrogen sulphate (0.3 g, 1 mmol), and sodium hydroxide solution (25 ml, 3M) was refluxed for 3 h. The organic layer was separated, dried ($MgSO_4$), washed through a plug of silica with dichloromethane (200 ml), and concentrated in vacuo. The residues were distilled to give the title compound as a colourless, viscous oil (8.0 g, 88%) bp 110° C. at 0.1 mm Hg. NMR ($CDCl_3$, 250 MHz) δ=2.26 (2H,q,J=6 Hz), 3.77 (2H,t,J=6 Hz), 4.13 (2H,t,J=6 Hz), 6.90–7.00 (3H,m), 7.26–7.34 (2H, m).

(b) Preparation of 1-(4-(3-chloropropoxy)phenyl)-2-phenyl-1-butanone

3-Chloropropoxybenzene (8g, 47 mmol) was added to a stirred solution of 2-phenylbutyric acid (8.5 g, 52 mmol) in trifluoroacetic anhydride (7.5 ml, 52 mmol) and stirring continued for 16 h. The mixture was poured into saturated sodium bicarbonate solution (100 ml), neutralized by addition of sodium bicarbonate, and extracted with ethyl acetate (3×50 ml). The combined organic extracts were washed with water (2×50 ml), dried (MgSO$_4$), and concentrated in vacuo. The residues were distilled to give the title compound as a white waxy solid (12.01 g, 81%) bp 200° C. at 0.1 mm Hg.

NMR (CDCl$_3$, 250 MHz) δ=0.87 (3H,t,J=7.25 Hz), 1.87–1.90 (1H,m), 2.14–2.26 (3H,m), 3.70 (2H,t,J=6 Hz), 4.37 (1H,t,J=7.25 Hz), 6.61 (2H,d,J=10 Hz), 7.10–7.20 (1H,m), 7.14–7.28 (3H,m), 7.91 (2H,d,J=10 Hz).

IR (cm$^{-1}$) 2966, 2934, 1736, 1600.

MS(Fast atom bombardment)m/e=317 (M$^+$+1), 197(M$^+$−120)

(c) Preparation of E-1-(4-(3-chloropropoxy)phenyl)-1-(4-iodophenyl)-2-phenyl-1-butene To a stirred solution of 1,4,dilodobenzene (1.34 g, 4 mmol) in anhydrous tetrahydrofuran (5 ml) was added n-butyllithium (2.5 ml, 1.6M in hexane, 4 mmol) under N$_2$ at −78° C., and stirring was continued for one hour. A solution of 1-(4-(3-chloropropoxy)-phenyl)-2-phenyl-1-butanone (2.01 g, 4 mmol) in THF (10 ml) was added and the mixture was allowed to warm to room temperature. After 16 h the mixture was poured into ethyl acetate (50 ml) and washed with brine (50 ml), and water (2×50 ml). The organic layer was dried (MgSO$_4$), and concentrated in vacuo. The residues were dissolved in ethanol (20 ml) and concentrated hydrochloric acid (5 ml) was added. The mixture was refluxed for 3 h., poured into saturated sodium bicarbonate (50 ml) and extracted with ethyl acetate (3×50 ml). The organic layer was washed with water (2×50 ml), dried (MgSO$_4$) and concentrated in vacuo.

Recrystallisatton from ethanol gave the title compound as white crystals (0.698 g, 35%), mp 98°–100° C.

NMR (CDCl$_3$, 250 MHz) δ=0.92 (3H,t,J=7.26 Hz), 2.16 (2H,quin,J=6 Hz), 2.45 (2H,q,J=6 Hz), 3.69 (2H,t,J=6 Hz), 3.98 (2H,t,J=6 Hz), 6.55 (2H,d,J=10 Hz), 6.745 (2H,d,J=10 Hz), 6.99 (2H,d,J=10 Hz), 7.09–7.20 (5H,m), 7.675 (2H,d,J=10 Hz).

IR(cm$^{-1}$) 2965, 2929, 2871, 1605, 1508.

MS(Electon impact)m/e=502(M$^+$−1), 197(M$^+$−306) Analysis C$_{25}$H$_{24}$ClIO requires C 59.72, H 4.81, Cl 7.05, I 25.24; found C 59.94, H 4.86, Cl 7.03, I 25.28%

(d) Preparation of E-1-(4-(3-(N-pyrrolidino)propoxy)phenyl)-1-(4-iodophenyl)-2-phenyl-1-butene A mixture of E-1-(4-3-chloropropoxy)phenyl)-1-(4-iodophenyl)-2-phenyl-1-butene (0.25 g, 0.5 mmol), pyrrolidine (1 ml) and ethanol (5 ml) was refluxed for 4 h, then concentrated in vacuo. The residues were purified by flash chromatography (silica; eluant:ether) to give the product as an off-white solid (0.219 g, 82%), mp 84°–86° C.

NMR (250 MHz, CDCl$_3$) δ=0.90 (3H,J=7 Hz), 1.72–1.81 (4H,m), 1.95–2.0 (2H,m), 2.40–2.60 (8H,m), 3.88 (2H,t,J=6 Hz), 6.535 (2H,d,J=9 Hz), 6.72 (2H,d,J=9 Hz), 6.975 (2H, d,J=9 Hz), 7.05–7.10 (5H,m), 7.66 (2H,d,J=9 Hz).

MS(EI)m/e=537(M$^+$, 45%) Analysis C$_{29}$H$_{32}$NIO requires C 64.81, H 6.00, N 2.61, I 23.61; found C 65.00, H 6.10, N 2.56, I 23.20%

EXAMPLE 2

Preparation of E-1-(4-(3-(Dimethylamino)propoxy)phenyl)-1-(4-1iodophenyl)-2,phenyl-1-butene A mixture of E-1-(4-(3-chloropropoxy)phenyl)-1-(4-iodophenyl)-2-phenyl-1-butene (0.302 g, 0.6 mmol) and dimethylamine in methanol solution (20 ml, 30%) was heated in a sealed bomb at 100° C. for 2 h, then poured into ether (100 ml), and washed with brine (100 ml) and water (2×100 ml). The organic layer was dried (Na$_2$SO$_4$), and concentrated in vacuo. The residues were purified by flash chromatography (silica; eluant:ether) to give the title compound as an off-white solid (0.245 g, 81%), mp 106°–109° C.

NMR (250 MHz, CDCl$_3$) δ=0.89 (3H,t,J=7.3 Hz), 1.8–1.92 (2H,m), 2.2 (6H,s), 2.32–2.50 (4H,m), 3.85 (2H, t,J=6.4 Hz), 6.515 (2H,d,J=8.7 Hz), 6.70 (2H,d,J=8.7 Hz), 6.86 (2H,d,J=8.7 Hz) 7.05–7.20 (5H,m), 7.64 (2H,J=8.7 Hz).

MS(EI)m/e=511(M$^+$, 30%)

EXAMPLE 3

(a) Preparation of 4-chlorobutoxybenzene

A two phase mixture of phenol (5 g, 53 mmol), 1,4-dichlorobutane (30 ml), tetrabutylammonium hydrogen sulphate (0.3 g, 1 mmol), and sodium hydroxide solution (25 ml, 6M) was refluxed for 3 h. The organic layer was separated, dried (MgSO$_4$), and concentrated in vacuo. The residues were purified by flash chromatography (silica (Merck 15111); eluant:petrol) to give the product as a colourless viscous oil (7.57 g 77%) bp 250° C. at 0.2 mm Hg.

NMR (250 MHz, CDCl$_3$) δ=1.89–1.98 (4H,m), 3.60 (2H,t,J=75 Hz), 3.98 (2H,t,J=75 Hz), 6.85–6.95 (3H,m), 7.23–7.29 (2H,m).

(b) Preparation of 1-(4-(4-chlorobutoxy)phenyl)-2-phenyl-1-butanone

To a stirred solution of 2-phenylbutyric acid (5.6 g, 34 mmol) in trifluoroacetic anhydrlde (20 ml) was added 4-chlorobutoxybenzene (7.5 g, 41 mmol). After 16 h, the mixture was poured into saturated sodium bicarbonate solution (250 ml), and extracted with ether (2×100 ml). The combined organic layers were dried (MgSO$_4$), and concentrated in vacuo. The residues were purified by flash chromatography (silica; eluant:10–30% ethyl acetate in petrol) to give the title compound as an orange oil (10.6 g, 94% ).

NMR (250 MHz, CDCl$_3$) δ=0.88 (3H,t,J=7.35 Hz), 1.80–1.91 (4H,m), 2.12–2.24 (1H,m), 3.56–3.61 (2H,m), 3.98–4.02 (2H,m), 4.38 (2H,t,J=7.35 Hz), 6.83 (2H,d,J=9 Hz), 7.17–7.22 (1H,m), 7.23–7.29 (4H,m), 7.93 (2H,d,J=9 Hz).

IR(cm$^{-1}$) 2961, 1671, 1599, 1574

(c) Preparation of E-1-(4-(4-chlorobutoxy)phenyl)-1-(4-iodophenyl)-2-phenyl-1-butene To a stirred solution of 1,4-dilodobenzene (3.63 g, 11 mmol) in anhydrous tetrahydrofuran (30 ml) was added n-butyllithium (6.9 ml, 1.6M in hexane, 11 mmol) under N$_2$ at −78° C., and stirring was continued for 4 h. A solution of 1-(4-(4-chlorobutoxy)phenyl)-2-phenyl-1-butanone (3.3 g, 10 mmol) in tetrahydrofuran (20 ml) was added and the mixture was allowed to warm to room temperature. After 16 h the mixture was poured into saturated ammonium chloride solution (50 ml) and extracted with ether (50 ml). The organic layer was washed with water (2×50 ml), dried (MgSO$_4$), and concentrated in vacuo. The residues were dissolved in ethanol (100 ml) and concentrated hydrochloric acid (50 ml) was added. The mixture was refluxed for 2 h, poured into ether (200 ml), washed with water (2×50 ml). dried (MgSO$_4$), and concentrated in vacuo. The residues were purified by flash chromatography (silica; eluant:5–10% dichloromethane in petrol) to give a mixture of E and Z isomers of the title compound. Recrystallization from ethanol gave the E isomer title compound as white crystals (1.31 g, 25%), mp 85°–87° C.

NMR (250 MHz, CDCl$_3$) δ=0.84 (3H,t,J=7.5 Hz), 1.86–1.91 (4H,m), 2.425 (2H,q,J=7.5 Hz), 3.56 (2H,t,J=6 Hz), 3.84 (2H,t,J=6 Hz), 6.50 (2H,t,J=6.73 Hz), 6.71 (2H, d,J=6.73 Hz), 6.965 (2H,d,J=6.73 Hz), 7.07–7.19 (5H,m), 7.65 (2H,d,J=6.73 Hz).

MS( EI )m/e=516(M$^+$, 100%) Analysis: C$_{26}$H$_{26}$ClO requires C 60.42, H 5.07, Cl 6.86, I 24.55; found C 60.57, H 5.10, Cl 6.76, I 24.61%

(d) Preparation of E-1(4-(4-(N-pyrrolidino)butoxy)phenyl)-1-(4-iodophenyl)-2-phenylbutene A mixture of E-1-(4-(4-chlorobutoxy)phenyl)-1-(4-iodophenyl)-2-phenyl-1-butene (0.2 g, 0.4 mmol), pyrrolidine (2.5 ml) and ethanol (10 ml) was refluxed for 3 h, then poured into ether (75 ml), washed with water (3×50 ml), dried (MgSO$_4$), and concentrated in vacuo. The residues were purified by flash chromatography (silica; eluant:ether) to give the product as a colourless oil (0.131 g, 59%).

NMR (250 MHz, CDCl$_3$) δ=0.89 (3H,t,J=7.33 Hz), 1.57–1.80 (8H,m), 2.37–2.46 (6H,m), 3.81 (2H,t,J=6 Hz), 6.51 (2H,d,J=9 Hz), 6.70 (2H,d,J=9 Hz), 6.96 (2H,d,J=9 Hz), 7.06–7.18 (5H,m), 7.645 (2H,d,J=9 Hz).

MS(EI)m/e=550(M$^+$−1, 5%), 126(M$^+$−425, 100%), 84(M$^+$−467, 100%)

The title compound was dissolved in petrol and HCl gas bubbled through to give the hydrochloride salt as an off white solid. Analysis: C$_{30}$H$_{35}$NIO+½ H$_2$O requires C 65.34, H 6.21, N 2.35, I 23.01; found C 65.45, H 6.30, N 2.56, I 22.51%

EXAMPLE 4

Preparation of E-1-(4-(4-(Dimethylamino)butoxy)phenyl)-1-(4-iodophenyl)-2-phenyl-1-butene A mixture of E-1-(4-(4-chlorobutoxy)phenyl)-1-(4-iodophenyl)-2-phenyl-1-butene (0.429 g, 0.83 mmol) and dimethylamine in methanol solution (30 ml, 30%) was heated In a sealed bomb at 100° C. for 2 h, then poured into ether (75 ml), and washed with brine (100 ml) and water (2×100 ml). The organic layer was dried (Na$_2$SO$_4$), and concentrated in vacuo. The residues were purified by flash chromatography (silica; eluant:0–10% methanol in ether) to give the title compound as an off white solid (0.391 g, 89%) mp 74°–77° C.

NMR (250 MHz, CDCl$_3$) δ=0.89 (3H,t,J=7.3 Hz), 1.50–1.66 (2H,m), 1.66–1.79 (2H,m), 2.20(6H,s), 2.27 (2H, t,J=7.3 Hz), 2.415 (2H,q,J=7.3 Hz), 3.81 (2H,t,J=6.1 Hz), 6.505 (2H,d,J=8.7 Hz), 6.605 (2H,d,J=8.7 Hz), 6.965 (2H, d,J=8.7 Hz), 7.05–7.2 (5H,m), 7.635 (2H,d,J=8.7 Hz).

MS(EI)m/e=525(M$^+$, 1%).

EXAMPLE 5

(a) Preparation of 8-Chlorooctoxybenzene

A two phase mixture of phenol (5 g, 53 mmol), 1,8-dichlorooctane (25 ml), tetrabutylammonium hydrogensulphate (0.3 g, 1 mmol), and sodium hydroxide solution (25 ml, 6M) was refluxed for 16 h. The organic layer was separated, washed with water (2×50 ml), dried (MgSO$_4$), and concentrated in vacuo. The residues were columned (silica; eluant: dichloromethane/petrol 1:10) to give the title compound as a colourless mobile oil (9.20 g, 72%). bp 50° C. at 4.6 mm Hg. NMR (CDCl$_3$) δ=1.27–1.52 (8H, m), 1.70–1.81 (4H, m), 3.53 (2H,t,J=6 Hz), 3.93 (2H,t,J=6 Hz), 6.83–6.93 (3H,m), 7.00–7.10 (2H,m). IR (liq, cm$^{-1}$) 2992, 2937, 2858, 1601, 1587 MS(EI) m/e=240 (M$_+$, 1%)

(b) Preparation of 1-(4-(8-Chlorooctoxy)phenyl)-2-phenyl-1-butanone

8-Chlorooctoxybenzene (9.1 g, 38 mmol) was added to a stirred solution of 2-phenylbutyric acid (7.48 g, 46 mmol) in trifluoroacetic anhydride (7.5 ml, 52 mmol) and stirring continued for 16 h. The mixture was poured into saturated sodium bicarbonate solution (100 ml), neutralised by addition of sodium bicarbonate, and extracted with ether (2×100 ml). The combined organic extracts were dried (MgSO$_4$) and concentrated in vacuo. The residues were column-chromatographed (silica; eluant 5–10% dichloromethane in petrol) to give the title compound as a colourless oil (11.86 g, 81%). NMR (CDCl$_3$) δ=0.87 (3H,t,J=7.3 Hz), 1.26–1.50 (8H, m), 1.69–1.90 (5H,m), 2.08–2.26 (1H,m), 3.51 (2H,t,J=6.6 Hz), 3.94 (2H,t,J=6.6 Hz), 4.38 (1H,t,J=7.3 Hz), 6.83 (2H,d,J=8.8 Hz), 7.15–7.20 (1H,m), 7.20–7.28 (4H,m), 7.93 (2H,d,J=8.8 Hz). IR (liq, cm$^{-1}$) 2933, 2858, 1673, 1600, 1574, 1510 MS(Chemical Ionisation)m/e=387 (M$^+$+1, 10%)

(c) Preparation of E-1-(4-(8-chlorooctoxyphenyl)-1-(4-iodophenyl)-2-phenyl-1-butene To a stirred solution of 1,4-diiodobenzene (9.9 g, 30 mmol) in anhydrous tetrahydrofuran (100 ml) was added n-butyllithium (18.75 ml, 1.6M in hexanes, 30 mmol) dropwise under N$_2$ at −78° C., and stirring was continued for 15 min. A solution of 1-(4-(8-chlorooctoxy-phenyl)-2-phenyl-1-butanone (11.18 g, 29 mmol) in tetrahydrofuran (50 ml) was added and stirring continued at −78° C. for 2 h. Then the mixture was allowed to warm to room temperature. After 16 h, the mixture was quenched with saturated ammonium chloride solution (10 ml), poured into ether (100 ml) and washed with brine (50 ml) and water (2×50 ml). The organic layer was dried (MgSO$_4$), and concentrated in vacuo. The residues were dissolved in ethanol (100 ml), concentrated hydrochloric acid (50 ml) was added and the mixture was refluxed for 4 h. The ethanol was removed in vacuo, the residues were dissolved in ether (50 ml), washed with water (3×50 ml), dried (MgSO$_4$) and concentrated in vacuo. The residues were column-chromatographed (silica; eluant: 10% dichloromethane in petrol) to give a mixture of the title compound and the Z Isomer as a viscous colourless oil (13.6 g). Crystalisation from ethanol gave the title compound as white crystals (5.35 g, 31%) mp 64°–66° C. NMR (CDCl$_3$) δ=0.89 (3H,t,J=7.5 Hz), 1.26–1.46 (8H, m), 1.60–1.80 (4H, m), 2.415 (2H,q,J=7.4 Hz), 3.50 (2H,t,J=6.6 Hz), 3.79 (2H,t,J=6.6 Hz), 6.505 (2H,d,J=8.7 Hz), 6.705 (2H,d,J=8.7 Hz), 6.965 (2H,d,J=8.4 Hz), 7.07–7.19 (5H,m), 7.65 (2H,d, J=8.2 Hz). IR (evap, cm$^{-1}$) 2931, 2857, 1606, 1509. MS(CI) m/e=574 (M$^+$+1, 10%) Analysis C$_{30}$H$_{34}$ClIO requires C 62.89, H 5.98, Cl 6.19, I 22.15; found C 66.92, H 5.95, Cl 6.30, I 22.05%

(d) Preparation of 1-(4-(8-(N-pyrrolidino)octoxy)phenyl-1-(4-iodophenyl)-2-phenyl-1-butene A mixture of E-1-(4-(8-Chlorooctoxyphenol)-1-(4-iodophenyl-2-phenyl-1-butene (2.0 g, 3.5 mmol), pyrrolidine (15 ml) and ethanol (75 ml) was heated in a bomb at 100° C. for 4 h and then concentrated in vacuo. The residues were purified by flash chromatography (silica; eluant: ether) to give the title compound as a slightly brown oil (1.92 g, 90%). Crystallisation from MeOH gave pale brown crystals, mp 55°–58° C. NMR (CDCl$_3$) δ0.89 (3H,t,J=7.4 Hz), 1.22–1.55 (10H, m), 1.60–1.80 (6H,m), 2.31–2.50 (8H,m), 3.78 (2H,t,J=6.5 Hz), 6.51 (2H,d,J=8.7 Hz), 6.705 (2H,d,J= 8.6 Hz), 6.965 (2H,d,J=8.2 Hz), 7.07–7.19 (5H,m), 7.645 (2H,d,J=8.2 Hz). MS(CI) m/e=608 (M$^{30}$ +1, 35%) Analysis C$_{34}$H$_{47}$NIO requires C 67.21, H 6.97, N 2.31, I 20.89; found C 67.16, H 6.94, N 2.30, I 20.69

EXAMPLES 6 & 7

Preparations of E-1-(4-(4-N-pyrrolidino and 4-dimethylamino) butoxy)phenyl)-1-(3-iodophenyl)-2-phenylbutene

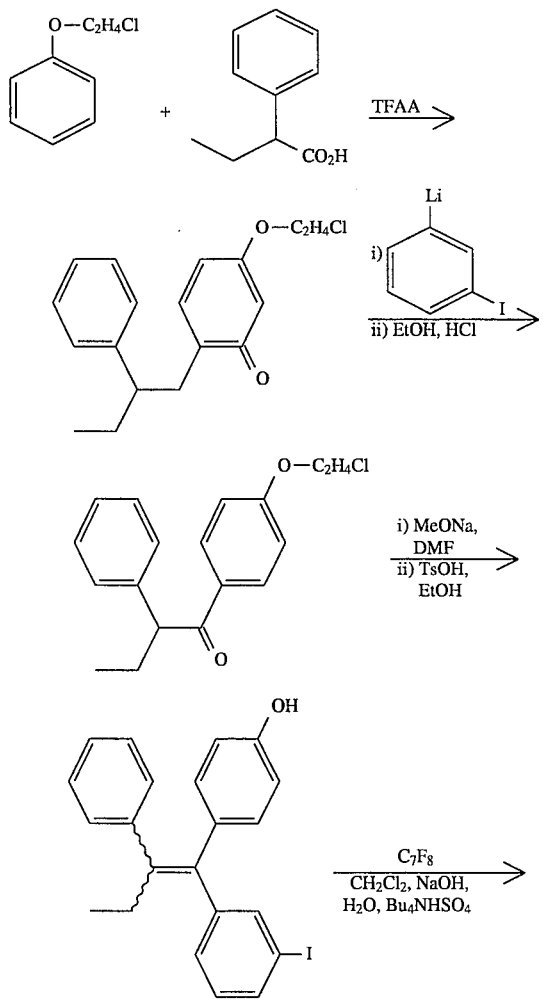

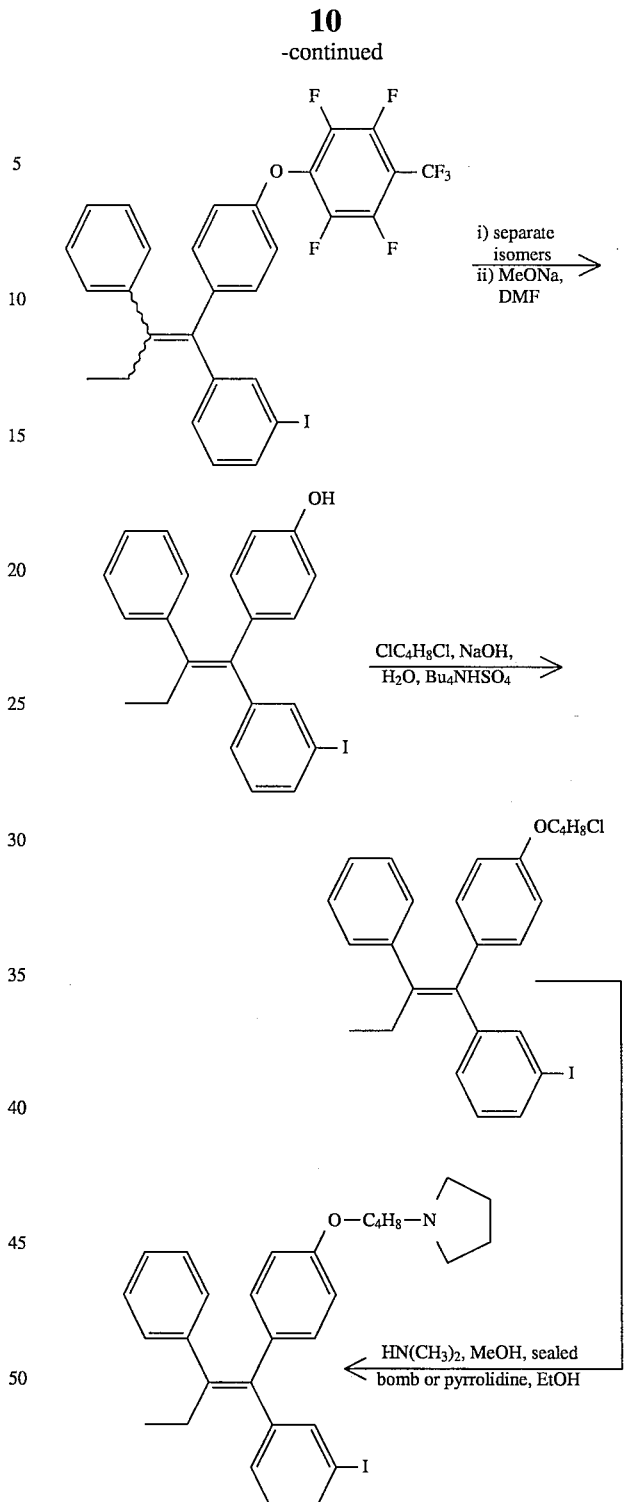

The 4-(2-chloroethoxy)ketone is prepared by the usual method. Reaction thereof with 3-iodophenyllithium gives the alcohol (not shown) which is dehydrated to give a mixture of E+Z isomers of the olefin. Reaction with sodium methoxide in DNF followed by treatment with toluenesulfonic acid in refluxing ethanol gives the phenolic compound as a mixture of E+Z isomers. Then phase-transfer reaction with octafluorotoluene gives the perfluorotolyl compound which allows separation of the isomers by chromatography or crystallization. Deprotection is accomplished by treatment with sodium methoxide in DMF and phase transfer reaction of the resulting phenolic compound with an α, ω-dichloroalkane (here $ClC_4H_8Cl$) gives the chloroalkoxy compound (here, 4-chlorobutoxy). Reaction with pyrrolidine or dimethylamine in the usual fashion provides the desired title compounds.

EXAMPLE 8

The compounds of formula (2) prepared in Examples 1–5, were tested for their efficacy in inhibiting the activation of cyclic AMP phosphodiesterase (cAMP-PDE) by calmodulin, which is believed to be an important requirement in improving the inhibition of oestrogen-responsive breast cancer cell growth. For some compounds, cytotoxicity against the MCF-7 human breast cancer cell line was determined. The test methods used were those described by M. G. Rowlands et al., Biochemical Pharmacology 40, 283–289 (1990). The relative binding affinity (RBA) for the oestrogen receptor (ER) was measured in a rat uterine cystosol competitive binding assay as described by A. E. Wakeling, 1987 (Chapter 7 p219–236 in "STEROID HORMONES—A PRACTICAL APPROACH" Eds B. Green and R. E. Leake, IRL Press Ltd, Oxford, UK). For comparison, 17β-estradiol has a RBA of 100.

TABLE

| Test Compound | Short Term in vitro cytotoxicity MCF-7 IC50 (μM) ± SD | Antagonism of calmodulin dependent cAMP-PDE IC50 (μM) ± SD | Binding affinity for ER RBA |
|---|---|---|---|
| Tamoxifen (comparative) | 14.00 ± 1.00 | 6.75 ± 1.06 | 4 |
| 4-iodotamoxifen (comparative) | 7.63 ± 0.06 | 2.30 ± 0.42 | Not Done * |
| 4-iodo compounds of formula (2): | | | |
| n = 3, $R^1 = R^2$ = CH3 | Not Done | 2.02 ± 0.17 | Not Done |
| n = 4, $R^1 = R^2$ = CH3 | Not Done | 2.25 ± 0.18 | 25 |
| Idoxifene (comparative) | 7.27 ± 0.38 | 1.45 ± 0.08 | 17 |
| 4-iodo compounds of formula (2): | | | |
| n = 3, $NR^1 = R^2$ = pyrrolidino | 4.50 ± 0.07 | 1.11 ± 0.07 | 23 |
| n = 4, $NR^1 = R^2$ = pyrrolidino | 3.99 ± 0.60 | 1.01 ± 0.08 | 9 |
| n = 8, $NR^1 = R^2$ = pyrrolidino | Not Done | 0.26 ± 0.05 | 4 |

*The RBA of 4-iodotamxifen was not measured in these experiments since comparative values with Idoxifene and tamoxifen have been reported twice before in the literature. Thus R. McCague, G. Leclercq, N. Legros, J. Goodman, G. M. Blackburn, M. Jarman and A. B. Foster, J. Med. Chem. 32, 2527–2533 (1989) reported the following values for RBA with receptor from calf uterine cytosol (oestradiol = 100)
tamoxifen = 1
Idoxifene = 5
iodotamoxifen = 5
S. K. Chander, R. McCague, Y. Luqmani, C. Newton, M. Dowsett and R. C. Coombes, Cancer Research 51, 5851–5858 (1991) report RBAs for rat uterine receptor:
tamoxifen = 5
Idoxifene = 12.5
iodotamoxifen = 12.5

The results, shown in the Table, include figures for tamoxifen, 4-iodotamoxifen and its pyrrolidino analogue, Idoxifene. It will be seen that in the cAMP-PDE test that the inhibiting concentration required is reduced in the compounds of formula (2) compared with the corresponding prior art compounds. The MCF-7 cytotoxicity data also shows a lowering of the concentration required compared with the prior art compounds.

We claim:

1. Compounds of the general formula

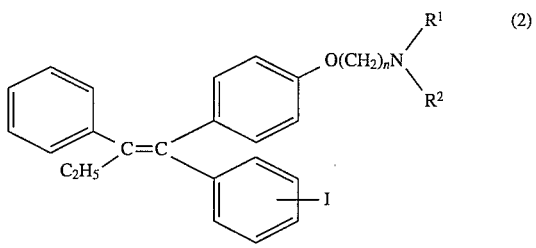

(2)

wherein n is an integer of from 3 to 8, the iodo substituent is in the 3- or 4-position and $R^1$ and $R^2$, which may be the same or different, represent $C_{1-3}$ alkyl groups or $R^1$ represents a hydrogen atom and $R^2$ a $C_{1-3}$ alkyl group or $R^1$ and $R^2$ together with the nitrogen atom to which they are attached represent a saturated heterocyclic group, in the form of their free bases or pharmaceutically acceptable acid addition salts.

2. Compounds according to claim 1 wherein $R^1$ and $R^2$ represent methyl groups or $R^1$ and $R^2$ together with the said nitrogen atom represent a pyrrolidino group.

3. Compounds according to claim 1 wherein the iodo substituent is in the 4-position.

4. Compounds according to claim 1, wherein n is 3 or 4.

5. Compounds according to claim 1 wherein the iodine atom is radioisotopic.

6. Compounds according to claim 5 wherein the iodine atom comprises $^{125}I$.

7. Compounds according to claim 5 wherein the iodine atom comprises $^{123}I$ or $^{131}I$.

8. Compounds according to claim 2 wherein the iodo substituent is in the 4-position.

9. A pharmaceutical composition comprising a compound according to claim 1 in association with a pharmaceutically effective diluent, carrier or excipient.

10. A method of treating a patient suffering from an estrogen-dependent cancer, which method comprises the step of administering to the patient an effective dose of a compound according to claim 1.

11. A method according to claim 10 wherein the estrogen-dependent cancer is a breast cancer.

12. A method according to claim 10 wherein the iodine atom of the compound administered is $^{125}I$.

13. A method of diagnosis of tumor cells which contain estrogen receptors, said method comprising the step of administering to the patient an amount of a compound according to claim 13 effective to provide a gamma ray image of said cells and making a diagnosis based on said image.

* * * * *